US011050278B1

(12) United States Patent
Townsend, III et al.

(10) Patent No.: US 11,050,278 B1
(45) Date of Patent: Jun. 29, 2021

(54) METHODS AND SYSTEMS FOR CHARGING AND MONITORING ELECTRONIC DEVICES IN CONFINEMENT INSTITUTIONS

(71) Applicant: Confinement Telephony Technology, LLC, Greensboro, NC (US)

(72) Inventors: John Vincent Townsend, III, Kernersville, NC (US); Rick Allen Lubbehusen, Winston Salem, NC (US); Jeffrey Adam Livaudais, Summerfield, NC (US); Timothy Edwin Pabon, Greensboro, NC (US); Johnnie Richard Tayloe, Rural Hall, NC (US)

(73) Assignee: CONFINEMENT TELEPHONY TECHNOLOGY, LLC, Greensboro, NC (US)

( * ) Notice: Subject to any disclaimer, the term of this patent is extended or adjusted under 35 U.S.C. 154(b) by 207 days.

(21) Appl. No.: 16/429,698

(22) Filed: Jun. 3, 2019

Related U.S. Application Data

(60) Provisional application No. 62/682,241, filed on Jun. 8, 2018.

(51) Int. Cl.
*H02J 7/00* (2006.01)
*G10L 17/00* (2013.01)
*A61L 2/10* (2006.01)
*A61L 2/24* (2006.01)
*G06K 9/00* (2006.01)

(52) U.S. Cl.
CPC ............. *H02J 7/0045* (2013.01); *A61L 2/10* (2013.01); *A61L 2/24* (2013.01); *G06K 9/00255* (2013.01); *G06K 9/00288* (2013.01); *G10L 17/00* (2013.01); *H02J 7/0021* (2013.01); *A61L 2202/11* (2013.01)

(58) Field of Classification Search
None
See application file for complete search history.

(56) References Cited

U.S. PATENT DOCUMENTS

| 2016/0188933 A1* | 6/2016 | Powell | G06K 7/10881 |
| | | | 235/462.42 |
| 2016/0342874 A1* | 11/2016 | Powell | G06K 7/0004 |

(Continued)

FOREIGN PATENT DOCUMENTS

| CN | 103826906 B | * 10/2016 | .......... B60L 11/1846 |
| CN | 107026492 A | * 8/2017 | |

(Continued)

*Primary Examiner* — Mohammed Rachedine
(74) *Attorney, Agent, or Firm* — Thompson Hine LLP

(57) ABSTRACT

Implementations disclosed herein provide a charging station configured to attach to or be positioned adjacent to a wall in a confinement institution and to simultaneously charge multiple tablets, mobile phones, laptops, or other portable electronic devices. In some implementations, the charging station is configured with protective sides that may help protect inserted electronic devices from damage. The charging and use of the electronic devices within the confinement institution may be automatically managed based connections at the charging stations, communications with the electronic devices, audio, images, or video of the electronic devices or users captured cameras on the charging station or the electronic devices, and/or information provided by the users.

24 Claims, 14 Drawing Sheets

(56) References Cited

U.S. PATENT DOCUMENTS

2016/0375783 A1* 12/2016 Uyeki .................... B60L 53/65
                                                        320/137
2017/0004340 A1*  1/2017 Powell ............... G06K 7/10732
2018/0351375 A1* 12/2018 Baldasare ............. H02J 7/0047

FOREIGN PATENT DOCUMENTS

| CN | 206961247 U | * | 2/2018 |
| CN | 210743087 U | * | 6/2020 |
| TW | 201909095 A | * | 3/2019 |
| TW | 201909095 A | * | 3/2019 |

* cited by examiner

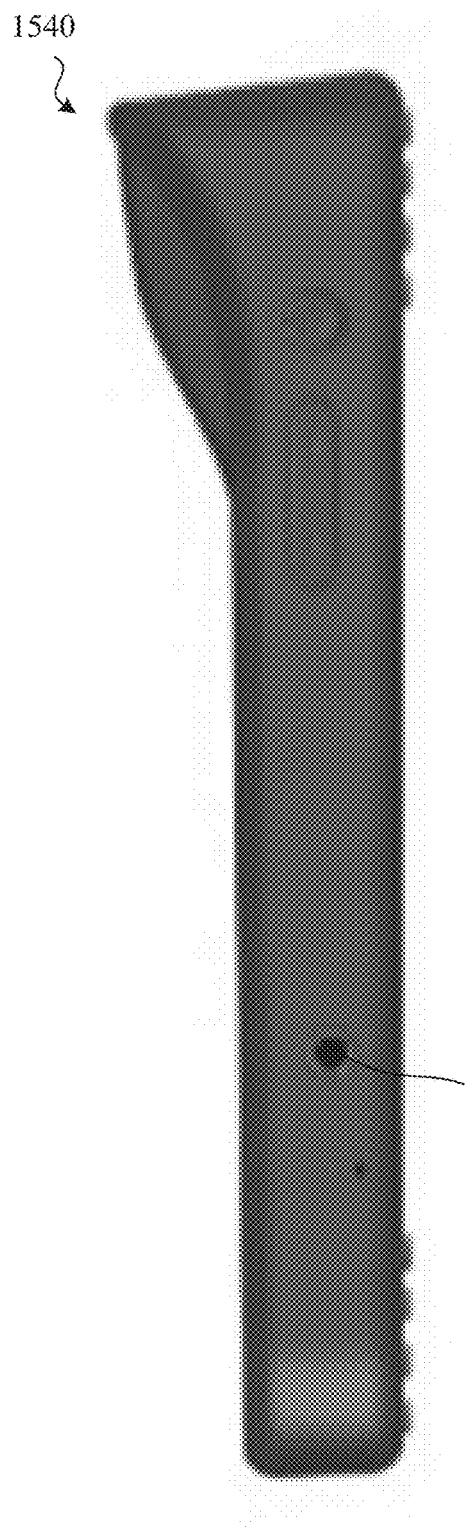
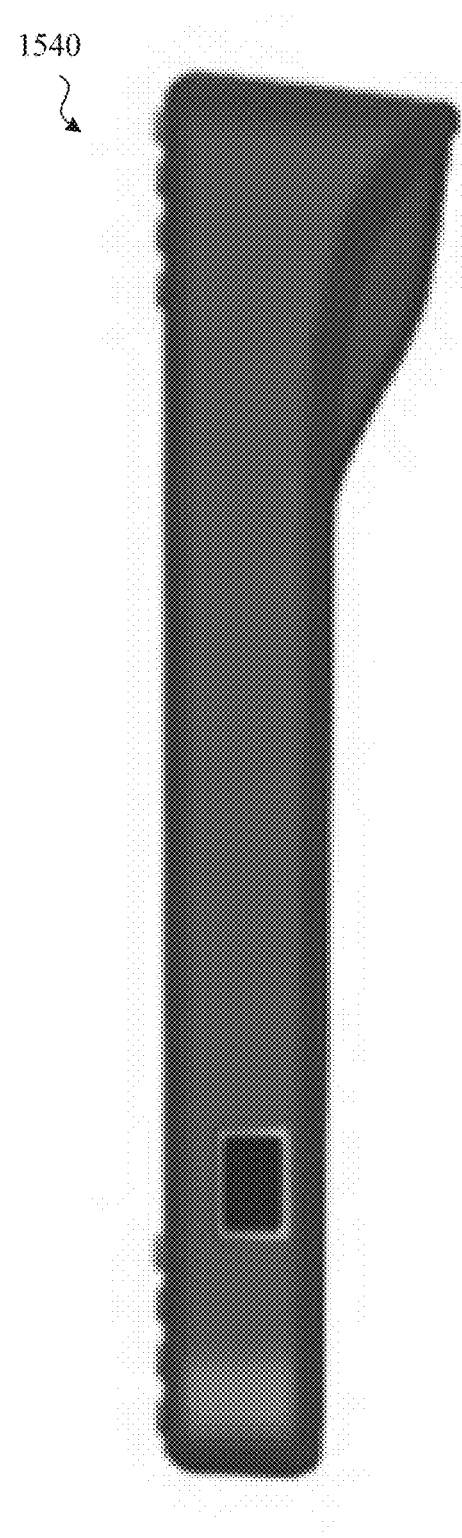
FIG. 20  FIG. 21

METHODS AND SYSTEMS FOR CHARGING AND MONITORING ELECTRONIC DEVICES IN CONFINEMENT INSTITUTIONS

CROSS-REFERENCE TO RELATED APPLICATION

This application claims the benefit of U.S. Provisional Application Ser. No. 62/682,241 filed Jun. 8, 2018, which is incorporated herein in its entirety.

FIELD OF THE INVENTION

This disclosure relates generally to electronic devices, systems, and methods used in confinement institutions, including devices, systems, and methods that are used to charge tablets and other electronic devices and perform various other useful functions in confinement institutions.

BACKGROUND

Confinement institution inmates have traditionally had very limited access to telephones and other electronic devices. Recently, confinement institutions have begun allowing inmates to use tablets and other mobile electronic devices. Charging such devices presents numerous challenges in the context of confinement institutions, and existing cord-based and cart-based charging systems generally do not adequately account for inmate safety, space limitations, security, and other concerns in these environments. The dispersion and collection of electronic devices within confinement institutions also presents challenges. Officers of the institution may be able to assist with dispersion and collection of electronic devices in some circumstances. However, the availability of officers to do so is generally limited significantly by the demands on the time of the officers for other duties. It is also generally desirable to avoid accessories (e.g., wires, USB storage devices, etc.) and the use of cords as such accessories and cords may increase the time and effort required to address the charging, dispersion, and collection of devices in confinement institutions. In addition, various safety risks are associated with cords.

SUMMARY

As described above, existing cord-based and cart-based charging systems generally do not adequately account for inmate safety, space limitations, security, and other concerns. Implementations disclosed herein provide a charging station configured to attach to or be positioned adjacent to a wall or bars in a confinement institution and to simultaneously charge multiple tablets, mobile phones, laptops, or other portable electronic devices. The charging station can be configured with a slim profile, for example, in some implementations extending from the wall less than 6 inches, less than 12 inches, less than 18 inches, or less than 24 inches. Such a slim profile may be less likely to interfere with doors, corridor traffic, and room usage and may make the charging station less likely to be damaged. In some implementations, a slim profile charging station is configured to use significantly less space that a cart-based or box charger and is suitable for installation in narrow hallways and rooms with various space constraints.

In some implementations, a charging station is configured with protective sides that may help protect inserted electronic devices (e.g., tablets) from damage. For example, a charging station may include a rack that includes a back and one or more structures that form a row of slots extending a first distance from the back. The back may have one or more mounting components, e.g. for mounting on a wall or vertical bars. The row of slots may be angled relative to a vertical orientation of the rack, may have pins to properly align electronic devices during insertion, may have magnets to secure electronic devices, may have power connections, may have electrical contacts/pins on their bottoms or sides, and/or may have contactless charging mechanisms. The slots may have openings in bottom portions, for example, to allow water or trash to fall through without clogging up the inside of the slots or preventing charging.

The charging station has sides adjacent to the row of slots and extending a second distance from the back. The second distance (e.g., of the sides) may greater than the first distance (e.g., of the slots). The relatively shorter first distance that the row of slots extends may be configured so that portions of inserted electronic devices are exposed and thus easily accessible to be grasped or otherwise easily inserted and removed. The relatively greater second distance that the sides extend from the back may be configured so that the exposed portions of the electronic devices are protected, e.g., by extending as far or farther than the electronic devices extend from the back.

In some implementations, the slots and the electronic devices are shaped such that each of the electronic devices fits in a slot in only a single orientation. Each of the electronic devices may have a bump portion such that it fits in a slots in only a single orientation. Such a bump portion of an electronic device may be configured to provide an angled viewing surface when the electronic devices is resting on a horizontal surface.

In some implementations, a charging station includes indicators (e.g., lights) that indicate electronic devices changing charging status of one or more electronic devices and/or that indicate that one or more electronic devices are correctly or incorrectly seated in the slots.

In some implementations, a charging station has a lock for securing a plurality of electronic devices. For example, a charging station may include a locking pin, bar, or roll top cover that prevents removal of one or more electronic devices. In some implementations, electronic devices can be returned to but not released from the charging station when the lock is in a locked state.

Some implementations provide devices, systems, or methods that track a user (e.g., inmate) checking out or checking in an electronic device, e.g., from a charging station. In some implementations, a method is performed by a computing device such as a charging station device or a device communicatively coupled with a charging station device. The method identifies a charging station event at the charging station involving a user removing an electronic device from a receiving portion of the charging station (e.g., checking out a tablet) or the user returning the electronic device to the receiving portion of the charging station (e.g., checking in a tablet). In some implementations, the charging station event is detected based on detecting a power transfer connection being established or discontinued in the receiving portion.

The method further involves identifying the electronic device involved in the charging station event. In one example, the electronic device is identified based on receiving a scanned identifier (bar code) associated with the electronic device, e.g., a bar code on the electronic device itself. In another example, the electronic device is identified based on detecting that the electronic device has changed communication status with the charging station, e.g., connected to disconnected or vice versa, or changed charging status within an event time window, e.g., charging to not charging or vice versa. For example, the method may detect that only one device of ten electronic devices is no longer connected and thus infer that the device that is no longer connected must be the device that was checked out.

The method further involves identifying the user involved in the charging station event. In one example, the user (e.g., inmate) is identified based on an image of the user from a camera on the electronic device or a camera on the charging station at or within an event time window. In another example, the user is identified based on a thumbprint or other biometric reading captured by the electronic device or the charging station. In another example, the user is identified based on the user providing a personal identification number (PIN). In some implementations, a user interface on the charging station or electronic device guides the user through a checkin/checkout process to capture images and/or other information of the user and the electronic device.

The method also involves tracking use of the electronic device based on identifying the electronic device and the user involved in the charging station event. For example, this may involve determining a period of time that the device was checked out to a user, the applications or content used on the electronic device, the locations within the confinement facility that the electronic device was taken, power usage on the electronic device, data transmission usage on the electronic device, telephone calls made via the electronic device, video conference calls made via the electronic device, and any other usage of the electronic device that is relevant to a tracking system. In one implementation, tracking the use of the electronic device involves determining a period of time that the electronic device was used by the user based on a check-out charging station event and a check-in charging station event. The method may involve detecting a condition of the electronic device based on an image of the electronic device, e.g., comparing before and after images to identify damage.

Some implementations provide devices, systems, or methods that identify damage to an electronic device while it is checked out from a charging station. In some implementations, a method is performed by a computing device such as a charging station device or a device communicatively coupled with a charging station device. The method identifies a check-out charging station event at a charging station, the check-out charging station event involving a user removing an electronic device from a receiving portion of the charging station (e.g., checking out a tablet). The method involves identifying a check-in charging station event at the charging station, the check-in charging station event involving the user returning the electronic device to the receiving portion of the charging station; and (e.g., checking in a tablet). The method determines a change in condition of the electronic device based on a first condition of the electronic device at the check-out charging station event and a second condition of the electronic device at the check-in charging station event. The change may be determined based on images of the electronic device at the check-out charging station event and the check-in charging station event.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIG. 20 is a side view of another exemplary electronic device capable of being charged via a charging station.

FIG. 21 is a side view of the electronic device of FIG. 20.

Figure 1:
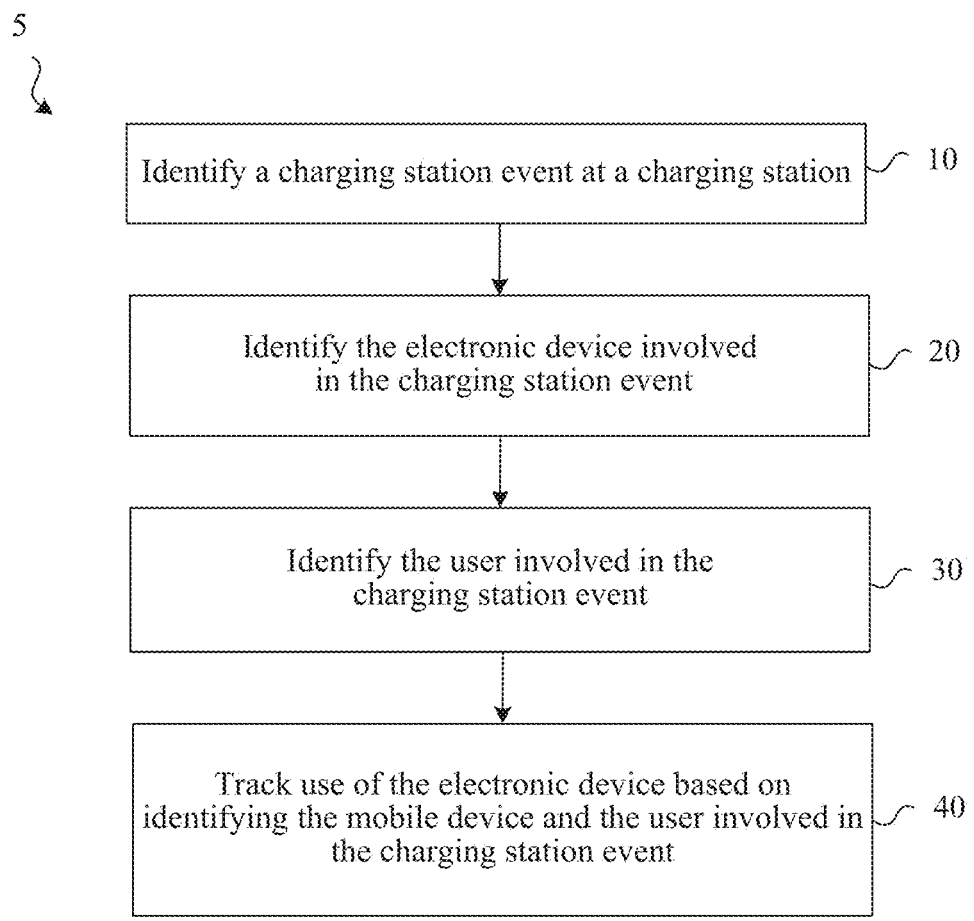
FIG. 1 is a flow chart illustrating an exemplary method of tracking use of an electronic device.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-systems, methods, components, devices and circuits have not been described in exhaustive detail so as not to obscure more pertinent aspects of the example implementations described herein.

FIG. 1 is a flow chart illustrating an exemplary method 5 of tracking use of an electronic device. In some implementations, the method 5 is performed by a device (e.g., charging station 100 or management unit 200 of FIGS. 3-5). The method 5 can be performed by a single device or multiple devices in communication with one another. In some implementations, the method 5 is performed by processing logic, including hardware, firmware, software, or a combination thereof. In some implementations, the method 5 is performed by a processor executing code stored in a non-transitory computer-readable medium (e.g., a memory).

At block 10, the method 5 identifies a charging station event at the charging station. The charging station has one or more receiving portions (e.g., charging slots) for charging one or more electronic devices simultaneously. The charging station event may involve a user removing an electronic device from a receiving portion of the charging station (e.g., checking out a tablet) or the user returning the electronic device to the receiving portion of the charging station (e.g., checking in a tablet). In some implementations, the charging station event is detected based on detecting a power transfer connection being established or discontinued in the receiving portion.

At block 20, the method 5 identifies the electronic device involved in the charging station event. The electronic device may be identified based on user input or an image, scan, or sound captured at the charging station. The electronic device may be identified based on an image of an identifier (e.g. a bar code) associated with the electronic device, e.g., a bar code on the electronic device itself. The electronic device may be identified based on a computer vision object detection of an image of the electronic device.

In another example, the electronic device is identified based on detecting that the electronic device has changed communication status with the charging station or changed charging status within an event time window—connected versus disconnected or charging versus not charging. For example, the method 5 may detect that only one device of ten or twelve devices has been disconnected within an event time window (e.g., within the last 30 seconds) and thus infer that the device that is no longer connected must be the device that was checked out. Similarly, the method 5 may detect that only one device of the ten or twelve devices has been connected within an event time window and thus infer that the device that was recently connected must be the device that was checked in. In some implementations, identifying an electronic device involves monitoring the charging status of a plurality of electronic devices and identifying that the electronic device is the only electronic device of the multiple electronic devices to change charging status within a charging event time window. If multiple electronic devices change charging status within the window, the method 5 may request additional input or user action (e.g., e.g., requesting that one of two devices that were disconnected be reconnected). In another example, only a single device is unlocked for a user to remove and the electronic device is identified based on that unlocking.

In some implementations, the electronic device is identified based on a communication received from the electronic device that identifies the device. For example, an electronic device may be configured to detect when its charging status changes and automatically send a message to the charging station or remote controller to provide notification of the change. In other examples, the electronic device sends a communication identifying the electronic device in response to another triggering events, e.g., the user providing input on the device, the device being detected within a particular area or threshold distance from the charging station or another reference point or device within the confinement institution, etc.

At block 30, the method 5 identifies which user was involved in the charging station event. In one example, the user (e.g., inmate) is identified based on an image of the user from a camera on the electronic device or a camera on the charging station at or within an event time window. In some implementations, the system stores a reference image or model of each of the multiple users who may access the electronic devices, captures one or more images of the environment around the charging station and/or electronic device during a charging station event time window, and performs a computer vision analysis, machine learning analysis, or computer-based algorithm to identify one or more individuals involved in the charging station event. In some implementations, multiple individuals are within the environment around the charging station during the charging station event time window and a computer vision technique, machine learning technique, or computer-based algorithm is used to select one of the multiple users as the user involved in the event. In some implementations, the user is identified based on performing computer vision-based face detection on an image of the user.

In some implementations, the user is identified based on creating a three dimensional model of the user using data obtained from an infrared projector and camera, an RGB-D camera, or another 3D model creation technique. A 3D model of one or more individuals near the charging station during a charging station event window may be compared with 3D models of individuals stored in a reference data set to identify those individuals.

In some implementations, multiple individuals are identified and the system provides instructions or receives input to identify which individual is involved in the charging station event, e.g., providing visual or audio content asking individuals not involved in the event to move away from the charging station in order to complete the event or asking the user for input to clarify which individual is involved in the event.

In some implementations, the user is identified based on a thumbprint or other biometric reading captured by the electronic device or the charging station. For example, the charging station and/or electronic device may prompt the user to provide a thumb print or hold the device up in front of the user's face so that an image of the user's face, eye, or other distinguishing physical characteristics can be captured and used for biometric-based identification.

In some implementations a user is identified by a voice sample that is recorded during a charging station event time window. Sounds in the environment may be separated based on a sound analysis to distinguish sounds near the charging station or electronic device from sounds farther away to distinguish the user involved in the charging station event from users and other sound sources not involved in the event. In some implementations, the user is asked to provide a voice sample during the charging station event, e.g., asked to say a particular word or phrase, to facilitate or improve the accuracy of sound-based user identification.

In some implementations, the user is identified based on the user providing a personal identification number (PIN), password, login credentials, or other user input at the charging station or on the electronic device.

In some implementations, for check-in type events the user is identified based on the electronic device. For example, the user may be determined to be the same user that currently has the electronic device checked out or that most recently checked out the electronic device.

In some implementations, a user interface on the charging station or electronic device provides visual or audible instructions to guide the user through a checkin/checkout process. The process may involve the user providing certain information or performing certain actions. The process may involve instructing the user so that appropriate images and/or other information of the user and/or the electronic device are received.

At block 40, the method 5 tracks use of the electronic device based on identifying the electronic device and the user involved in the charging station event. For example, this may involve determining a period of time that the device was checked out to a user, the applications or content used on the electronic device, the locations within the confinement facility that the electronic device was taken, power usage on the electronic device, data transmission usage on the electronic device, telephone calls made via the electronic device, video conference calls made via the electronic device, and any other usage of the electronic device that is relevant to a tracking system. In one implementation, tracking the use of the electronic device involves determining a period of time that the electronic device was used by the user based on a check-out charging station event and a check-in charging station event. The method may involve detecting a condition of the electronic device based on an image of the electronic device, e.g., comparing before and after images to identify damage.

Figure 2:
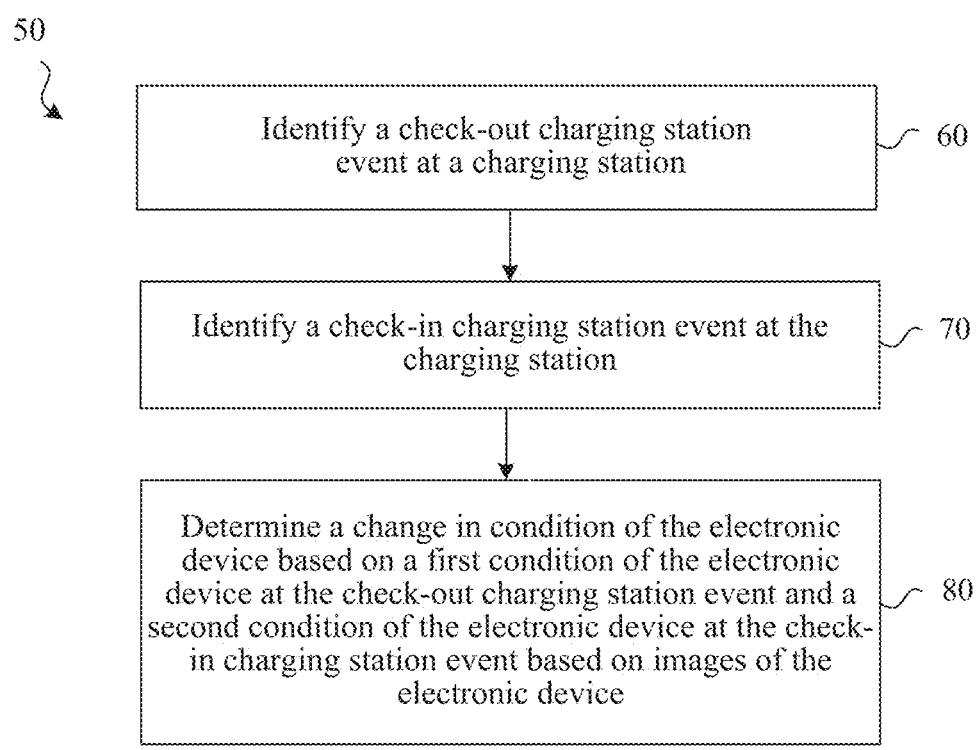
FIG. 2 is a flow chart illustrating an exemplary method of determining a change in condition of an electronic device.

FIG. 2 is a flow chart illustrating an exemplary method 50 of determining a change in condition of an electronic device. In some implementations, the method 50 is performed by a device (e.g., charging station 100 or management unit 200 of FIGS. 3-5). The method 50 can be performed by a single device or multiple devices in communication with one another. In some implementations, the method 50 is performed by processing logic, including hardware, firmware, software, or a combination thereof. In some implementations, the method 50 is performed by a processor executing code stored in a non-transitory computer-readable medium (e.g., a memory).

At block 60, the method 50 identifies a check-out charging station event at a charging station. The check-out charging station event may involve a user removing an electronic device from a receiving portion of the charging station (e.g., checking out a tablet). Identifying the event may involve identifying the user involved, the electronic device involved, and capturing information and images of the user, electronic device, and circumstances during an event window.

At block 70, the method 50 identifies a check-in charging station event at the charging station. The check-in charging station event may involve the user returning the electronic device to the receiving portion of the charging station. Identifying the check-in charging station event may involve identifying that a particular electronic device has been reconnected or reinserted into a slot of a charging station. Identifying the electronic device may be based by an electronic communication between the electronic device and the charging station, an image of the electronic device during an event window, and/or information provided by the user.

At block 80, the method 50 determines a change in condition of the electronic device based on a first condition of the electronic device at the check-out charging station event and a second condition of the electronic device at the check-in charging station event. The change may be determined based on images of the electronic device at the check-out charging station event and the check-in charging station event. For example, a computer vision technique may be used to score or evaluate the first condition of the electronic device at the check-out charging station event and a second condition of the electronic device at the check-in charging station event. In some implementations, a user is instructed to hold, position, or move the electronic device in view of a camera so that images or video of the electronic device from multiple perspectives are captured. In some implementations, scratches, dents, cracks, or other physical damage to exterior surfaces of the electronic device are identified. In some implementations, a machine learning process is used to evaluate the conditions or change in condition of the electronic device, e.g., using a neural network trained using images of electronic devices in various conditions (e.g., good, cracked, dented, etc.) In some implementations, the conditions of the electronic device are determined based on diagnostic software executed on the electronic device or charging station at the time of the check-out and check in charging station events.

In some implementations, the user is guided through an evaluation process in which the user provides explanations or comments about the electronic device. For example, the user may be asked to identify any defects or other issues with the electronic device at checkout. The user need not be responsible for defects and other issues that were present prior to the inmate's checking out the device and may be given the opportunity to identify such issues that are not otherwise automatically detected. As another example, the user may be asked to provide an explanation for any defects or other issues with the electronic device that are identified at check-in.

Exemplary Multi-Device Charging/Monitoring System

Figure 3:
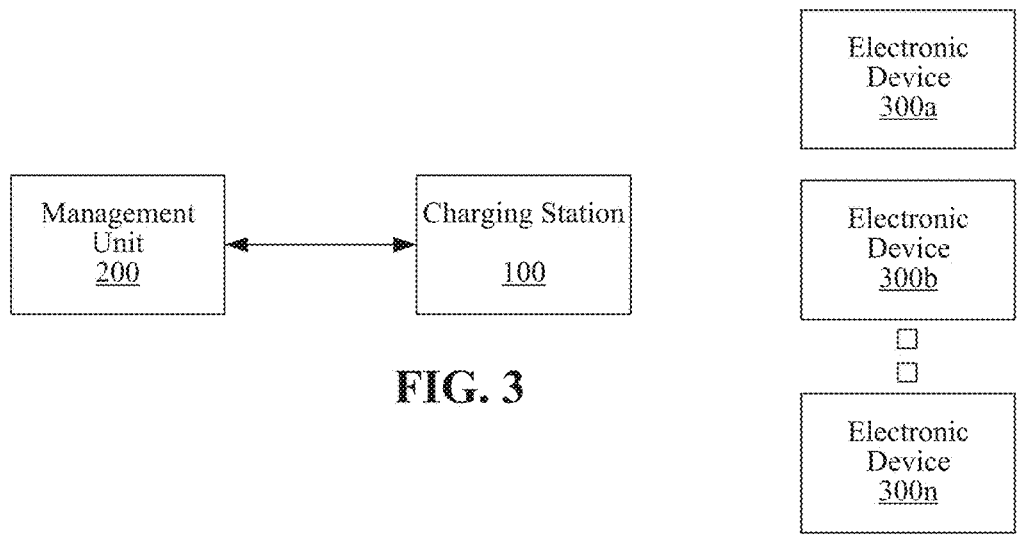
FIG. 3 is a block diagram of an example environment for certain implementations disclosed herein.
Figure 4:
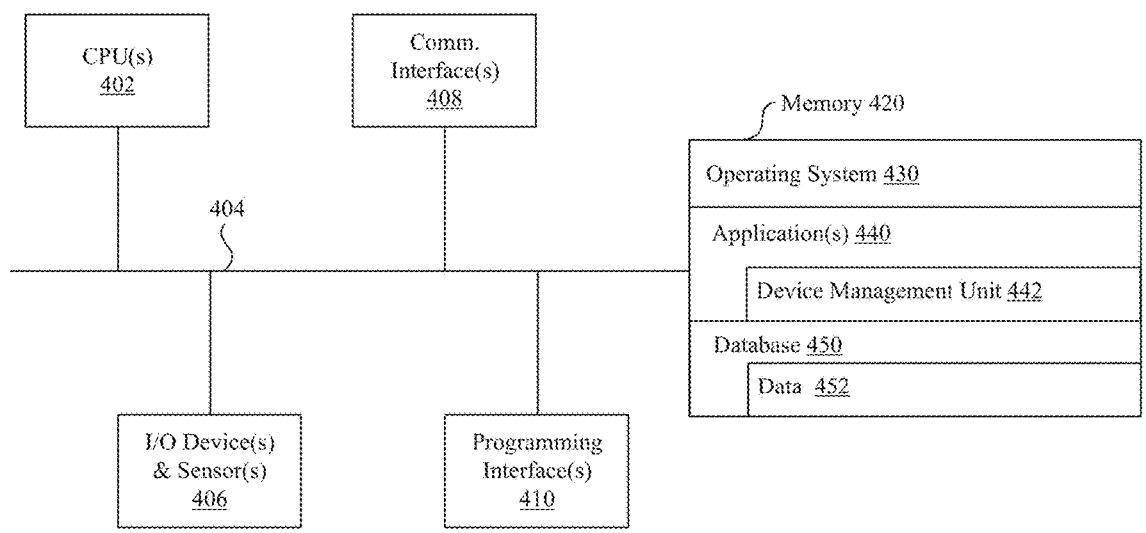
FIG. 4 is a block diagram of computing components of an example charging station.
Figure 5:
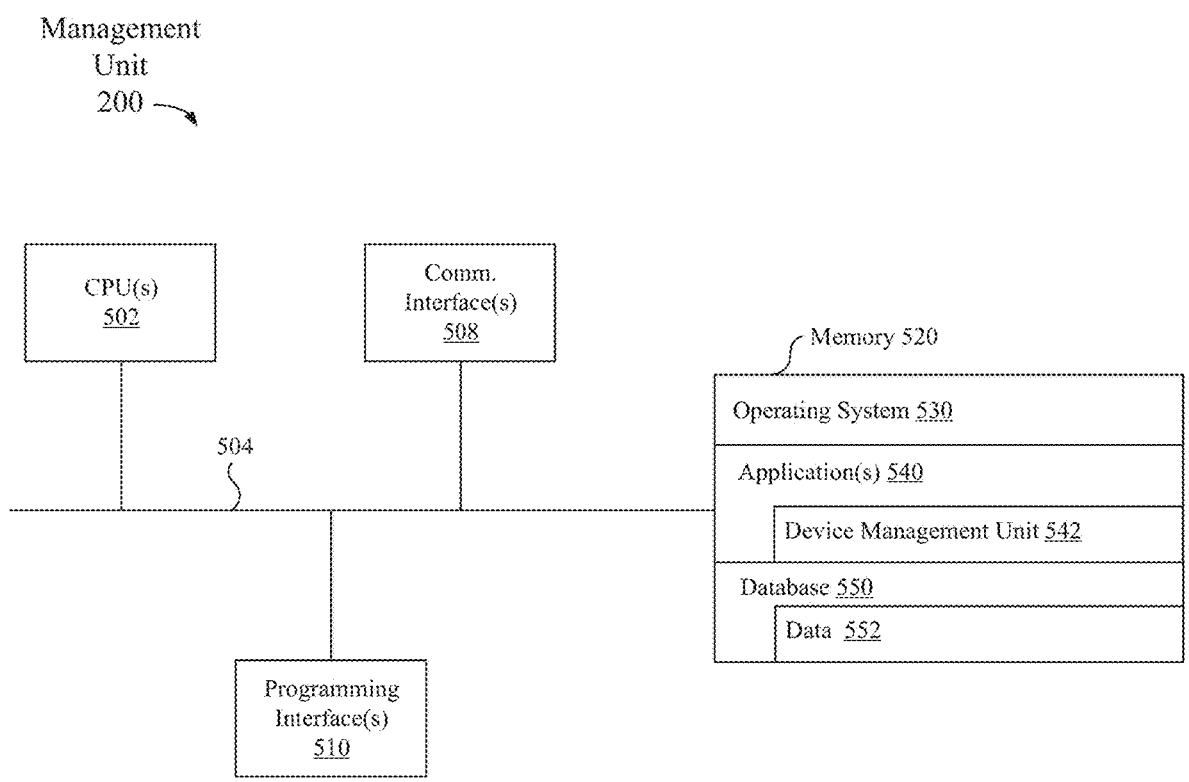
FIG. 5 is a block diagram of computing components of an example management unit.

FIGS. 3-5 illustrate an example environment for certain implementations disclosed herein. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the environment includes a charging station 100 and management unit 200, one or both of which may be in a confinement institution.

In some implementations, the management unit 200 is configured to manage and coordinate the charging and use of electronic devices 300a-n at the charging station 100 within the confinement institution. In some implementations, the management unit 200 includes a suitable combination of software, firmware, or hardware. The management unit 200 is described in greater detail below with respect to FIG. 3.

In some implementations, the management unit 200 is a computing device that is local or remote relative to the confinement institution. In one example, the management unit 200 is a desktop computer used by confinement institution personnel. In one example, the management unit 200 is a local server located within the confinement institution. In another example, the management unit 200 is a remote server located outside of the confinement institution (e.g., a cloud server, central server, etc.). In some implementations, the management unit 200 is communicatively coupled with the charging station 100 via one or more wired or wireless communication channels (e.g., BLUETOOTH, IEEE 802.11x, IEEE 802.16x, IEEE 802.3x, etc.).

In some implementations, the charging station 100 is configured to charge multiple electronic devices 300a-n simultaneously. In some implementations, the charging station 100 includes a suitable combination of software, firmware, or hardware for itself managing the charging and use of the electronic devices 300a-n. The charging station 100 is described in greater detail below with respect to FIG. 2. In some implementations, the functionalities of the management unit 200 are provided by or combined with the charging station 100, for example, in the case of charging station that functions as a stand-alone unit.

The electronic devices 300a-n may include processing units (e.g., microprocessors, ASICs, FPGAs, GPUs, CPUs, processing cores, or the like), input/output (I/O) devices and sensors, communication interfaces (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, or the like type interface), programming (e.g., I/O) interfaces, displays, image sensor systems, memory, and communication buses 504 for interconnecting these and various other components. The I/O devices and sensors may include an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), or the like. Information from the I/O devices and sensors may be communicated to the charging station 100 and/or management unit 200 to facilitate the charging and management of the electronic devices 300a-n.

FIG. 4 is a block diagram of an example of the charging station 100 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the charging station 100 includes one or more processing units 402 (e.g., microprocessors, application-specific integrated-circuits (ASICs), field-programmable gate arrays (FPGAs), graphics processing units (GPUs), central processing units (CPUs), processing cores, or the like), one or more input/output (I/O) devices 406, one or more communication interfaces 408 (e.g., universal serial bus (USB), FIREWIRE, THUNDERBOLT, IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, or the like type interface), one or more programming (e.g., I/O) interfaces 410, a memory 420, and one or more communication buses 404 for interconnecting these and various other components.

In some implementations, the one or more communication buses 404 include circuitry that interconnects and controls communications between system components. In some implementations, the one or more I/O devices 406 include at least one of a keyboard, a mouse, a touchpad, a joystick, one or more microphones, one or more speakers, a thermometer, physiological sensors (e.g., blood pressure monitor, heart rate monitor, blood oxygen sensor, blood glucose sensor, etc.), one or more biometric sensors, one or more microphones, one or more speakers, one or more depth sensors (e.g., a structured light, a time-of-flight, or the like), one or more displays or touch screens, or the like.

The memory 420 includes high-speed random-access memory, such as dynamic random-access memory (DRAM), static random-access memory (SRAM), double-data-rate random-access memory (DDR RAM), or other random-access solid-state memory devices. In some implementations, the memory 420 includes non-volatile memory, such as one or more magnetic disk storage devices, optical disk storage devices, flash memory devices, or other non-volatile solid-state storage devices. The memory 420 optionally includes one or more storage devices remotely located from the one or more processing units 402. The memory 420 comprises a non-transitory computer readable storage medium. In some implementations, the memory 420 or the non-transitory computer readable storage medium of the memory 420 stores the following programs, modules and data structures, or a subset thereof including an optional operating system 430, applications 440, and database 450. The applications 440 can include on more applications, such as application 442, configured to facilitate charging and use of the electronic devices. The database 450 can include data 452 about the electronic devices, inmate users, non-inmate users (e.g., officers, police, counselors, lawyers, prisoner friends and family, etc.), the confinement institution layout, the confinement institution systems (e.g., electrical, communication, etc.), and any other information useful by the applications 440.

Although these modules and units are shown as residing on a single device (e.g., the charging station 100), it should be understood that in other implementations, any combination of these modules and units may be located in separate computing devices. Moreover, FIG. 4 is intended more as functional description of the various features which are present in a particular implementation as opposed to a structural schematic of the implementations described herein. As recognized by those of ordinary skill in the art, items shown separately could be combined and some items could be separated. For example, some functional modules shown separately in FIG. 4 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, or firmware chosen for a particular implementation.

FIG. 5 is a block diagram of an example of the management unit 200 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the management unit 200 includes one or more processing units 502 (e.g., microprocessors, ASICs, FPGAs, GPUs, CPUs, processing cores, or the like), one or more communication interfaces 508 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, or the like type interface), one or more programming (e.g., I/O) interfaces 510, a memory 520, and one or more communication buses 504 for interconnecting these and various other components.

In some implementations, the one or more communication buses 504 include circuitry that interconnects and controls communications between system components. The memory 520 includes high-speed random-access memory, such as DRAM, SRAM, DDR RAM, or other random-access solid-state memory devices. In some implementations, the memory 520 includes non-volatile memory, such as one or more magnetic disk storage devices, optical disk storage devices, flash memory devices, or other non-volatile solid-state storage devices. The memory 520 optionally includes one or more storage devices remotely located from the one or more processing units 502. The memory 520 comprises a non-transitory computer readable storage medium. In some implementations, the memory 520 or the non-transitory computer readable storage medium of the memory 520 stores the following programs, modules and data structures, or a subset thereof including an optional operating system 530, applications 540, and database 550. The applications 540 can include on more applications, such as application 542, configured to facilitate charging and use of the electronic devices. The database 550 can include data 552 about the electronic devices, inmate users, non-inmate users (e.g., officers, police, counselors, lawyers, prisoner friends and family, etc.), the confinement institution layout, the confinement institution systems (e.g., electrical, communication, etc.), and any other information useful by the applications 440.

Moreover, FIG. 5 is intended more as a functional description of the various features which are present in a particular implementation as opposed to a structural schematic of the implementations described herein. As recognized by those of ordinary skill in the art, items shown separately could be combined and some items could be separated. For example, some functional modules shown separately in FIG. 5 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, or firmware chosen for a particular implementation.

Exemplary Multi-Device Charging Station

Figure 6:
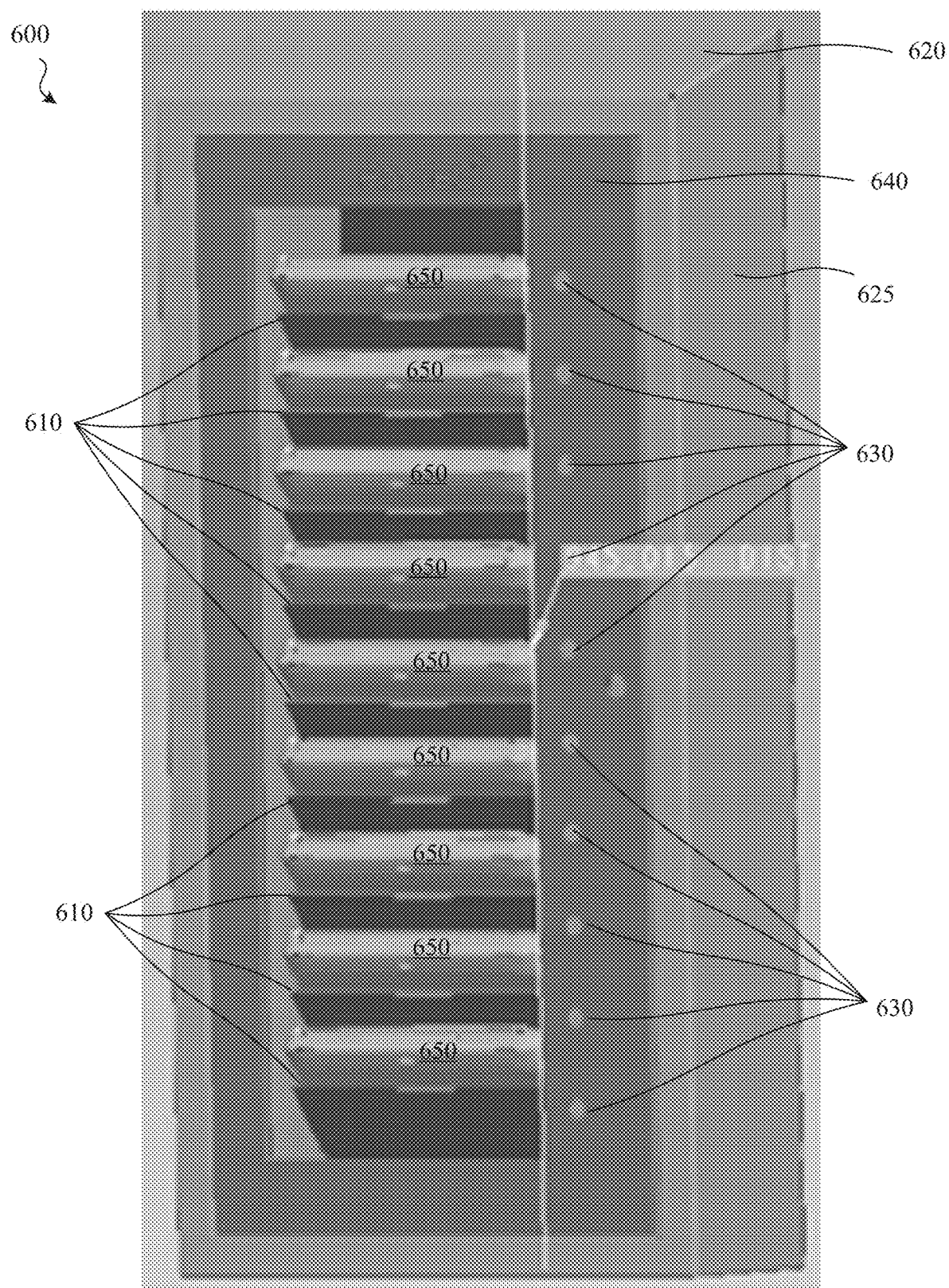
FIG. 6 is a perspective view of an example charging station.
Figure 7:
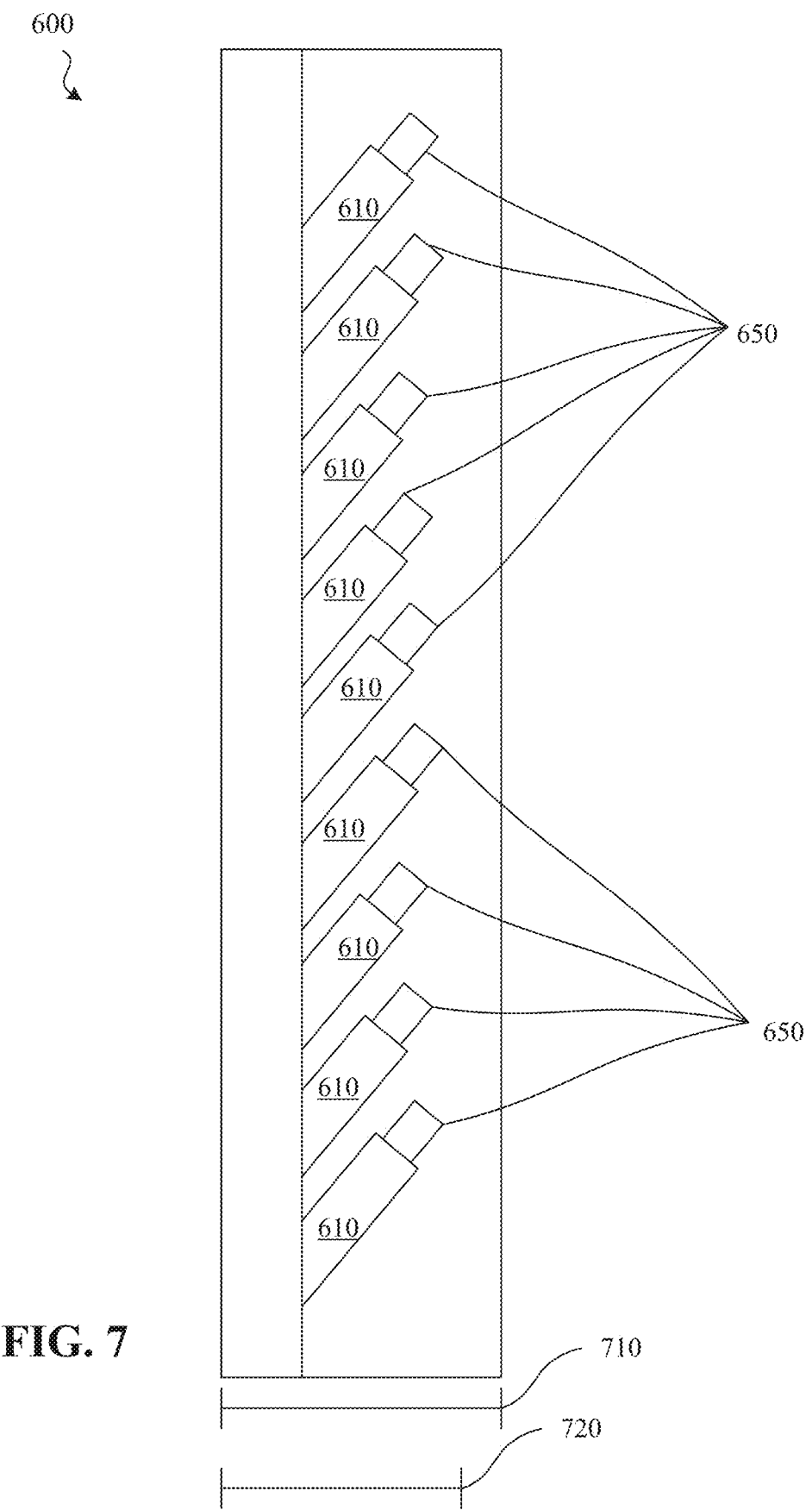
FIG. 7 is side view of the charging station of FIG. 6 with electronic devices inserted.
Figure 8:
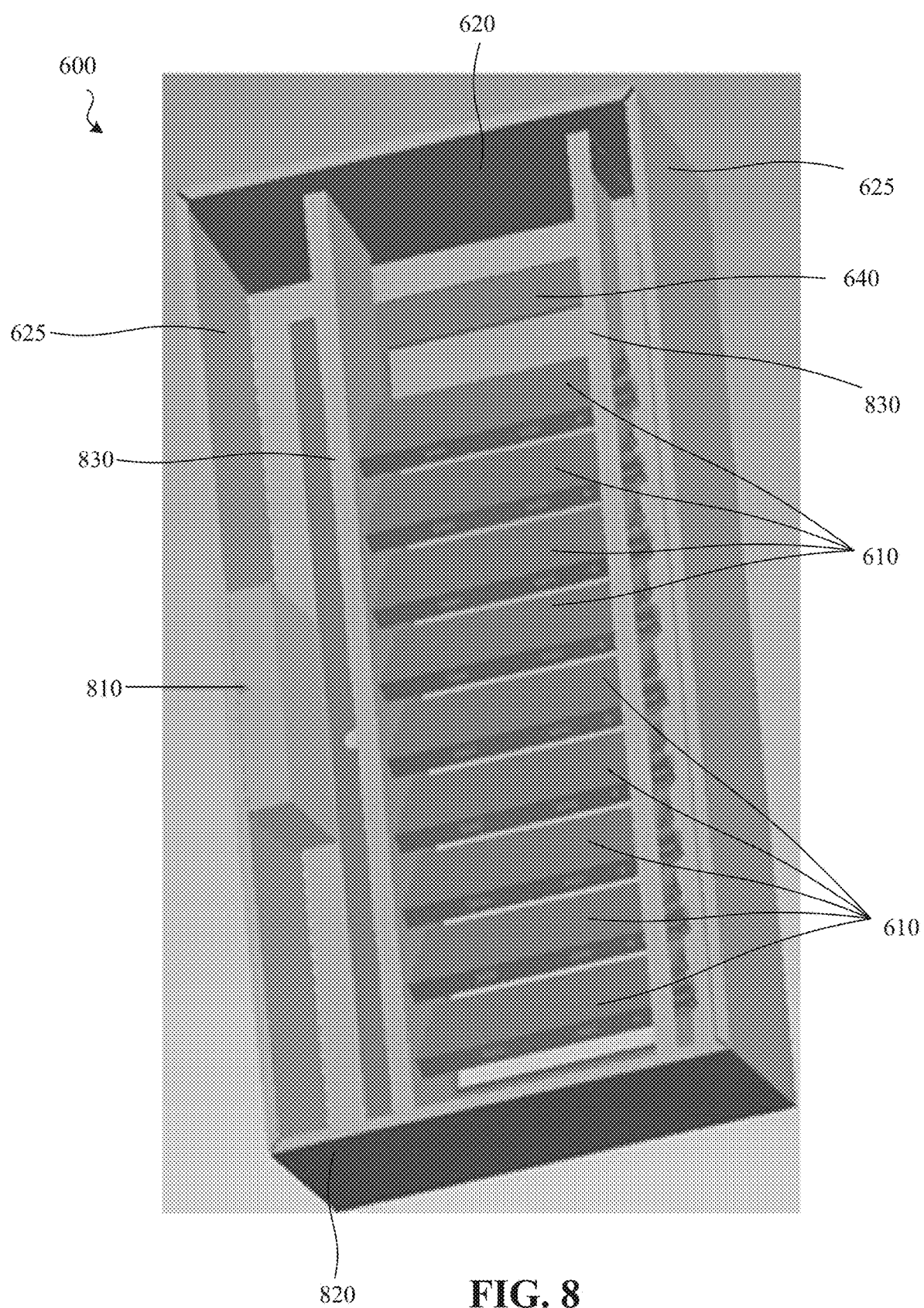
FIG. 8 is a perspective view of the charging station of FIG. 6.

FIGS. 6-8 illustrate an example charging station 600. The charging station 600 includes multiple slots 610 into which electronic devices 650 have been inserted for charging. The slots 610 are in a rack such that the slots 610 are angled relative to a vertical orientation of the rack. The slots may be supported by supports 830 (FIG. 8). The slots 610 may have pins to properly align electronic devices 650 during insertion. The slots 610 may have magnets to secure electronic devices 650. The slots 610 may have power connections, e.g., electrical contacts/pins on their bottoms or sides and/or contactless charging mechanisms. The use of non-plug-based and wireless electrical power mechanisms can provide significant advantages. Avoiding or limiting the use of plugs and wires is particular useful in the context of confinement institutions in which wires can be safety hazards and plugs may detract from device durability.

The slots 610 may have openings in bottom portions, for example, to allow water or trash to fall through without clogging up the inside of the slots or preventing charging.

The charging stations 600 is configured to attach to or be positioned adjacent to a wall in a confinement institution and to simultaneously charge multiple tablets, mobile phones, laptops, or other portable electronic devices 650. The charging station 600 is configured with a slim profile, for example, in some implementations extending from the wall less than 6 inches, less than 12 inches, less than 18 inches, or less than 24 inches. Such a slim profile may be less likely to interfere with doors, corridor traffic, and room usage and may make the charging station 600 less likely to be damaged. In some implementations, the charging station 600 is configured to use significantly less space that a cart-based or box charger and is suitable for installation in narrow hallways and rooms with various space constraints.

The charging station 600 is configured with protective features that may help protect inserted electronic devices 650 (e.g., tablets) from damage. The charging station 600 includes a casing including a top surface 620, side surface 625, and bottom surface 820 configured to enclose internal components 810, e.g., processors, memory, etc., and to protect electronic devices 650 that are inserted for charging. For example, the row of slots 610 with electronic devices 650 may extend a first distance 720 from the back and the charging station 600 may have sides, e.g., side surfaces 625, adjacent to the row of slots 610 and extending a second, greater distance 710 from the back. The slots 610 may be configured so that portions of inserted electronic devices 650 are exposed and thus easily accessible to be grasped or otherwise easily inserted and removed. The relatively greater second distance 710 may be configured so that the exposed portions of the electronic devices 650 are protected, e.g., by extending as far or farther than the electronic devices 650 extend from the back.

Indicators 630 are color lights that, in this example, indicate a charging status of each of the inserted electronic devices 650 (e.g., red indicates charging, green indicates fully charged, etc.) and/or that indicate that electronic devices 650 are correctly or incorrectly seated in the slots 610.

Front panel 640 on the front of the charging station 600 is configured to open to allow user access to the electronic devices 650. In this example, the front panel 640 includes a see-through portion or opening through which inserted electronic device 650 may be viewed while the front panel 640 is in a closed position.

In some implementations, the slots 610 and the electronic devices 650 are shaped such that the each of the electronic devices 650 fit in a slot in only a single orientation. Each of the electronic devices 650 may have a bump portion (see FIGS. 16-19) such that each electronic device 650 fits in a each of the slots 610 in only a single orientation.

Such a bump portion of an electronic device 650 may be configured to provide an angled viewing surface when the electronic device 650 is resting on a horizontal surface.

In some implementations, each electronic device 650 has an angled face on at least one side and thus side edges of unequal size, e.g., the bottom edge may be smaller than the right edge, left edge, and top edge. The only the smallest edge may fit into one of the slots 610 of the charging station 600, thus prohibiting an electronic device 650 from being inserted with any of the other three edges leading. In some implementations, the charging station 600 is configured to receive electronic devices 650 inserted only in a portrait orientation. In some implements, the charging station 600 is configured to receive electronic devices 650 inserted only in a landscape orientation.

In some implementations, a charging station 600 has a lock for securing a plurality of electronic devices 650. For example, the charging station 600 may include a locking pin, bar, or roll top cover that prevents removal of one or more electronic devices 650. In some implementations, electronic devices 650 can be returned to but not released from the charging station 600 when the lock is in a locked state.

In some implementations, the charging station 600 is configured for self-service by the individual inmates, controlling the electronic devices 650 such that an inmate is only able to remove an electronic device 650 after checking the electronic device out and tracking when the inmate returns the electronic device 650. The charging station 600 thus enables the controlled distribution and collection of electronic devices 650 without requiring significant officer supervision and time and ultimately conserving the confinement institutions resources.

Various components can be used to secure each electronic device 650 in a charging position and orientation. FIGS. 6-8 illustrates slots 650 into which electronic devices 650 can be received and securely held in a particular orientation (i.e., angled upwardly, or at any other angle). In this example, because of the orientation of the slots 610 and corresponding electronic devices 650, gravity helps secure each electronic device 650 in a respective slot 610 in electrical communication with a charging contact at the bottom of the slot 610. Each electronic device 650 can also have holes (e.g., two holes) that are designed to match up with pins. The holes and the pins seat together to align the electronic device 650 in the proper position.

Magnets can additionally or alternatively be used. In some implementations, the charging station 610 uses magnets to attract each electronic device 650 to the pins or charging contacts and hold each device firmly against such pins/contacts or otherwise securely within the charger. For example, upward facing magnets or metal contacts in the bottom of each slot 610 into which each electronic device 650 is received can magnetically interact with corresponding magnets or metal contacts on each electronic device 650.

The angled orientation of the slots 610 and corresponding electronic devices 650 (when inserted) reduces the required thickness of the charging station 600, e.g., enabling the charging station 600 to a have a slimmer (e.g., closer to the wall) profile than otherwise. In some implementations, the charging station 600 is configured to fold or otherwise transform to further reduce its profile or protect the electronic devices 650.

The charging station 600 can have various features that facilitate mounting to a wall including, but not limited to, fasteners, mounting brackets, screw holes, magnets, etc. In some implementations, a wall-mounted charging station rests on an underlying floor surface to provide all or some of its support. In other implementations, the charging station 600 does not rest on the floor and the mounting features provide sufficient support to retain the charging station 600 in a fixed position relative to the wall without floor support. In some implementations a wall-mounted charging station 600 is supported partially or entirely from a support that extends from a ceiling, overhanging beam, or other support. In some implementations, the charging station 600 can be raised and lowered, for example, to raise the charger and associated electronic devices 60 to minimize interference with facility space or restrict inmate access to the devices when not in use or during device-restricted time periods.

In some implementations, a charging station 600 is installed on cell bars, a mobile cart, or a vehicle.

In some implementations, one or more charging stations 600 are connected using a mounting bracket that allows technicians to service the unit(s) while still hanging on the wall/and or using a face frame that is easily removable (or hinged). In some implementations, the charging station 600 is mounted on a roll around cart, or standing cart, bars, or with an optional stand so it will sit on a table/floor or other flat surface.

Figure 9:
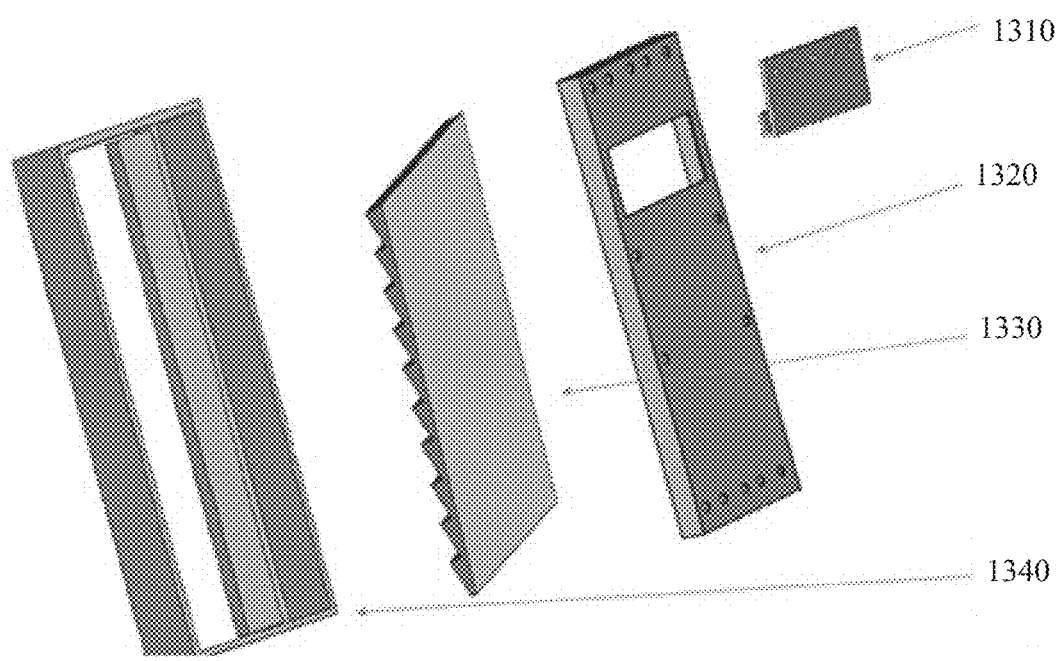
FIG. 9 is an exploded view of components of a charging station.
Figure 10:
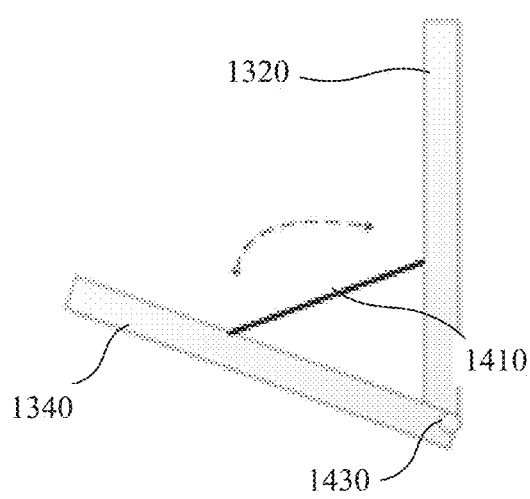
FIG. 10 is an exploded view of folding components of a charging station.
Figure 11:
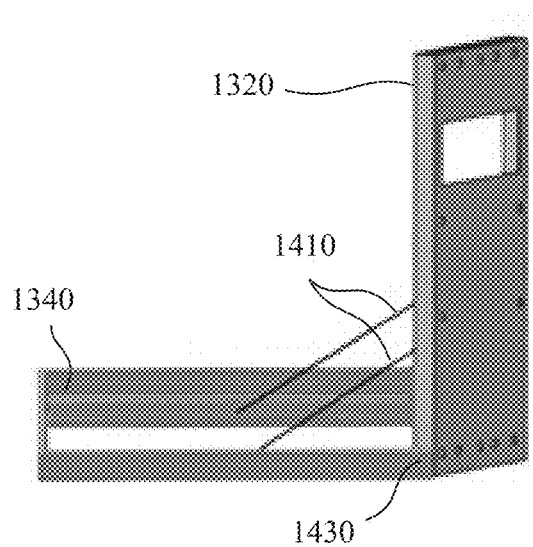
FIG. 11 is an exploded view of folding components of a charging station.
Figure 12:
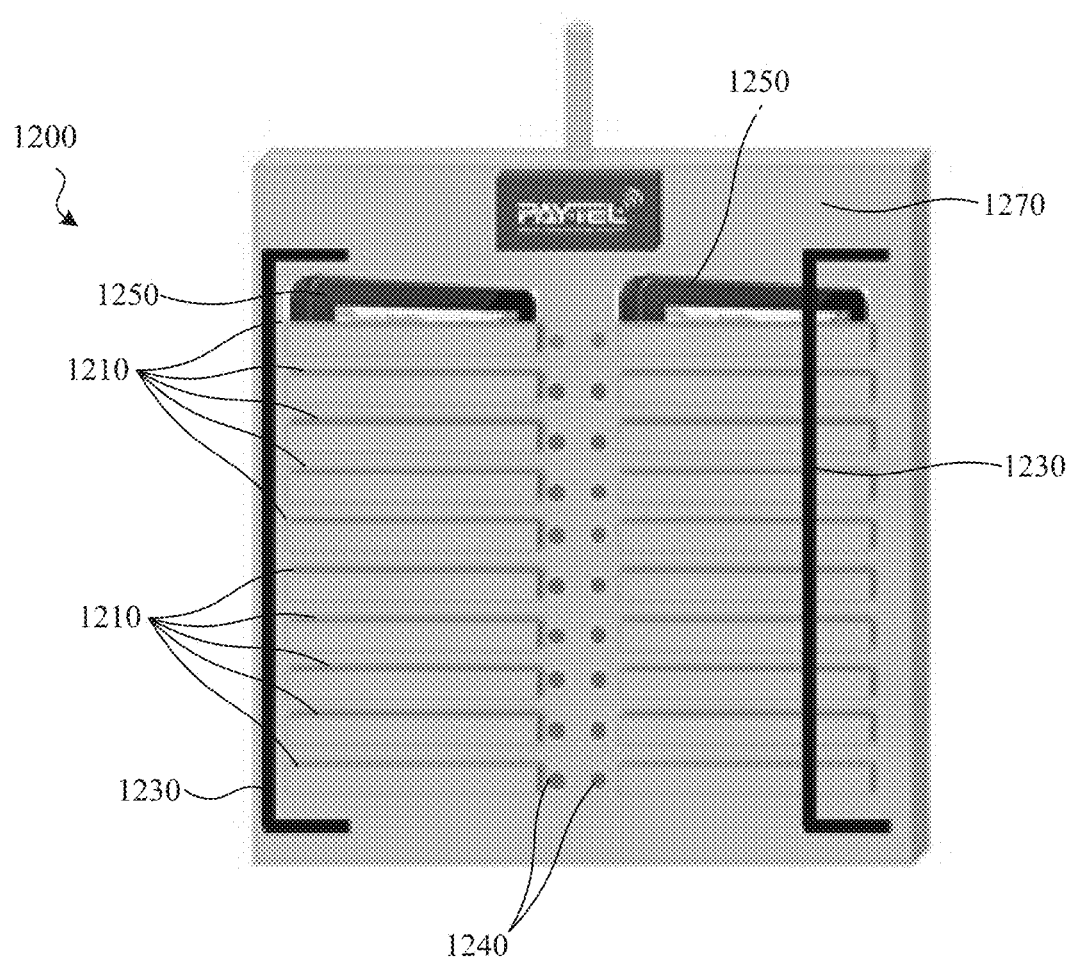
FIG. 12 is a front view of another example charging station.

In some implementations, a wall-mounted charging station is mounted to a confinement facility wall using a hanging plate. FIGS. 9-11 illustrate components for hanging a charging station. In this example, a hanging plate 1310 is configured with openings for screws, bolts, or other fasteners to be secured to a wall. The hanging plate 1310 will hold the charging station once installed. The back plate 1310 is configured with an opening that enables it to be installed over the hanging plate 1310. The back plate 1310 may also be fastened to the wall using screws, bolts, or other fasteners. The charging rack 1330 includes slots for charging electronic devices and is configured to be inserted into and supported by the back plate 1320. The charging rack 1330 may include wiring that is hidden behind the front cover 1340. The front cover 1340 attaches (e.g., via screws) to the back plate 1320 to provide protection and a finished appearance.

In some implementations, as illustrated in FIGS. 10 and 11, the front cover 1340 is attached via a hinge 1430 to make it easy for the charging station to be serviced. In one example, the charging station includes a mounting bracket installed on the wall. In this example, the front panel is able to swing away from the wall on the hinge 1430. This may enable a service technician to service the charging station without removing it from the wall upon which it is mounted. In some implementations, the hinges 1410 can be removed for service, for example, to enable removing some or all of the charger from the wall. The charging station can include another mechanisms that functions in conjunction with the hinges 1430 to limit the movement of the charging station on the hinges 1430. For example, the charging station includes cables 1410 configured to only allow the hinges 1430 to open far enough for service or to create a safe level platform for service. In other implementations, one or more of these functions is achieved with a service hanger that allows all items to hang on the wall without a hinge.

Cameras, microphones, and/or other features of the electronic devices may be used while the electronic devices are charging. In some implementations, the charging station is configured to ensure that each electronic device has a particular orientation as described above. In one such implementation, an electronic device only fits in the charger in one way, with the electronic device's camera facing out into the room away from the charging station. The electronic device is communicatively coupled (e.g., via WIFI) with another device, e.g., charging station 100 or management unit 200, that receives images from the camera on the electronic device at the charging station. In one example, a facility manager uses a management unit 200 to communicate with an electronic device in the charging station 100 to turn the electronic device's camera "on" to investigate what is happening near the electronic device. Microphones on the electronic device can also be remotely enabled to listen to the area. In some implementations, a microphone is enabled while the camera is being used in the charging station. Motion detection alerts could be sent to email, SMS, or any other appropriate device or person.

In some implementations, the charging station 100 or management unit 200 is configured to control an associated electronic device when an electronic device is being inserted into or removed from the charging station. A camera or other sensor on the electronic device is activated or otherwise used to capture an image or other information during the time when the electronic device is inserted into or removed from the charger. In one implementation, a camera captures an image of an inmate (or other person) inserting or removing an electronic device and facial recognition or person identification is used to identify the inmate/person who is automatically associated with the action. Accordingly, a system in this example is configured to track check-in/ check-out activities based on automatically detecting actions (e.g., device insertion and device removal) and automatically identifying the person associated with the action. Such as system can retain the images or other inmate/person identifying data for various purposes, for example, to rebut an assertion by an inmate that the inmate did not check-out/remove a given electronic device. In some implementations, the charging station is configured to unlock and allow removal of an electronic device after an image or other information is detected and used to identify which inmate is removing the device. Similarly, inserting a device can be controlled to only allow insertion after inmate identification is complete. Note that inmates can be identified based on RGB image data, RGB-D image data, infrared sensor, sound detection, retina detection, etc. along with a suitable algorithm and data for identifying an inmate. Inmate detection can be based on 2D/image based object detection or 3D/shape based object detection techniques.

In some implementations, the charging station includes a locking system/feature that enables facility staff to lock or unlock specific electronic devices, specific sets of electronic devices, or all electronic devices. Example locking mechanisms include, but are not limited to, sliding/rotating metal bars, roll-top type of locking covers, fold in locks that keeps electronic devices secure, locking pins that could be above the devices or slide into cavities in any side of the devices.

The locking mechanism can secure the electronic devices and prevent unauthorized access to or damage to the electronic devices. The locking system could be located on any side or face of the charging station. The locking mechanism can include one or both of a manual operation configuration or an electronic operation configuration that uses, for example, motors and electronics. The locking system can be configured to allow for the receipt of additional electronic devices even if the charging station is locked, and electronic devices are returned late.

Figure 13A:
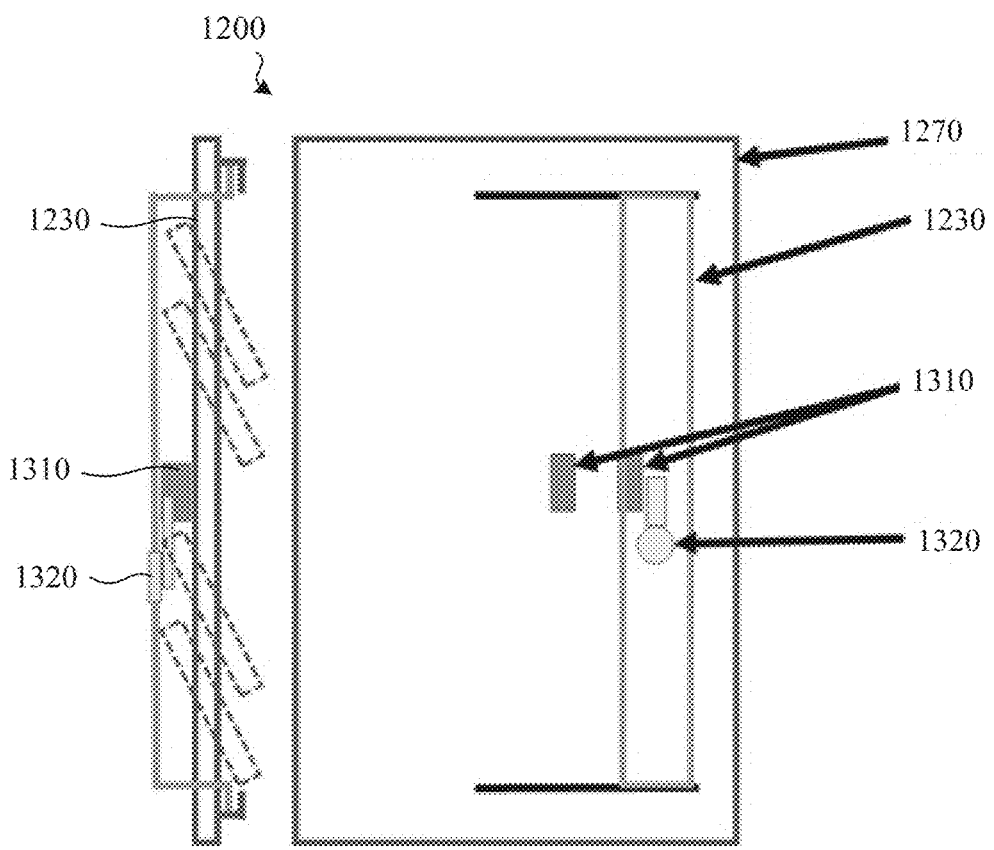
FIGS. 13A and 13B are block diagrams illustrating a locking mechanism of a charging station.
Figure 13B:
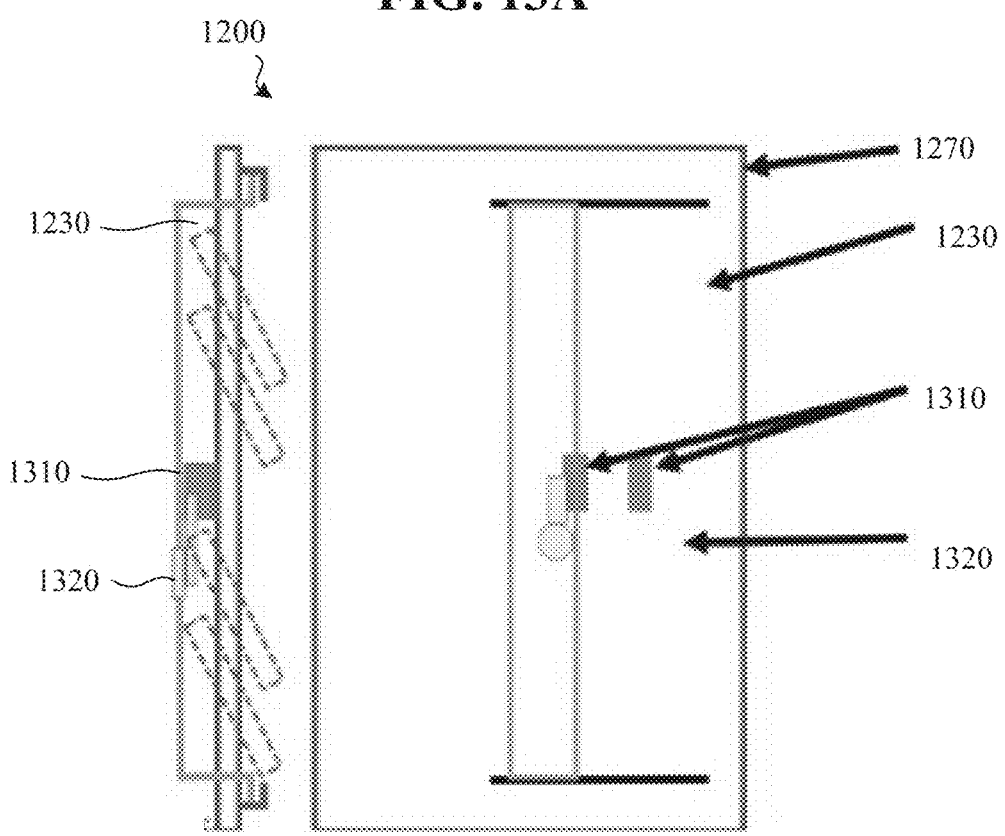
Figure 14:
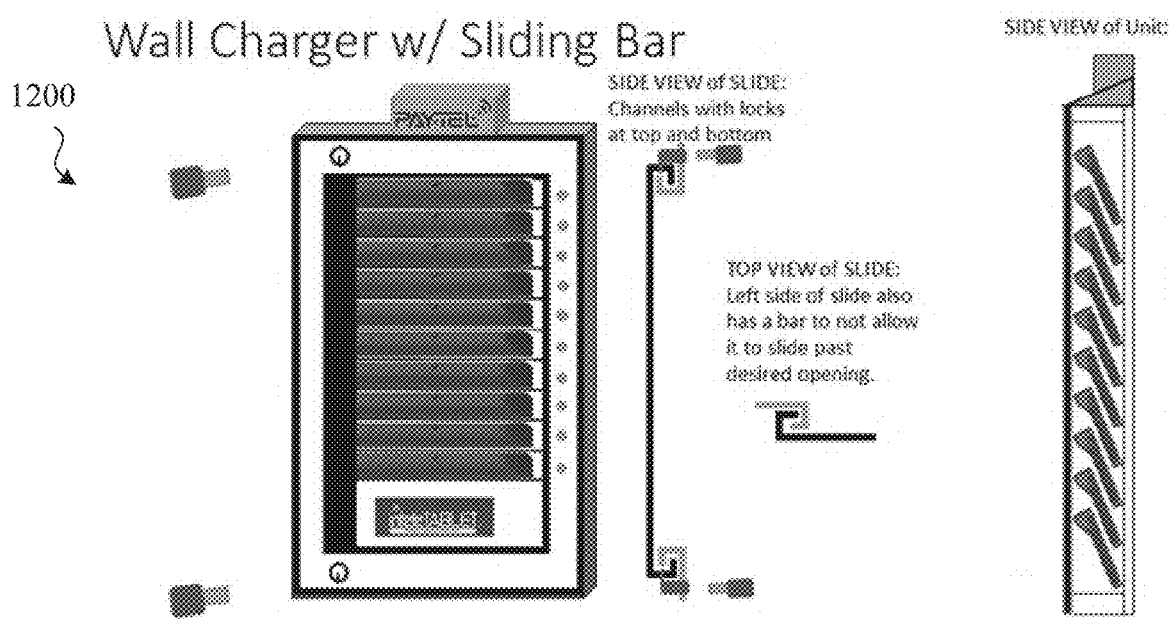
FIG. 14 is a block diagram illustrating a sliding bar locking mechanism of a charging station.

FIGS. 12, 13A, 13B, and 14 illustrate a charging station 1200 that includes slots 1210 for electronic device 1250 on fixed front panel 1270. Indicators 1240 are used to indicate charging/insertion status of the electronic devices 1250. In this example, locking bars 930 slide or rotate to secure the electronic devices 1250 within the slots 1210. In FIGS. 13A and 13B, a lock 1320 is mounted on locking bar 1230 and interacts with stops 1310. The lock 1320 will brace up against the one of the stops 1320 (e.g., the right stop) when the unit is unlocked as shown in FIG. 13A. When the unit is locked, the lock 1320 will brace up against the other of the stops 1310 (e.g., the left stop) and the locking bar 1230 would be in a more central position as shown in FIG. 13B, thus prohibiting the removal of any electronic devices.

Figure 15A:
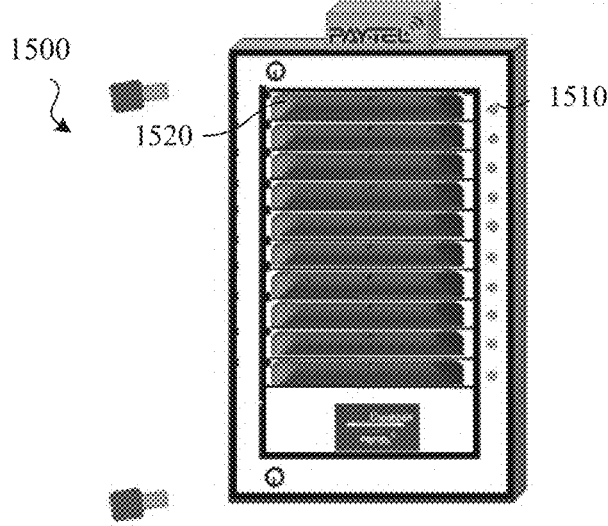
FIGS. 15A and 15B are block diagrams illustrating locking pin-based locking mechanism of a charging station.
Figure 15A:
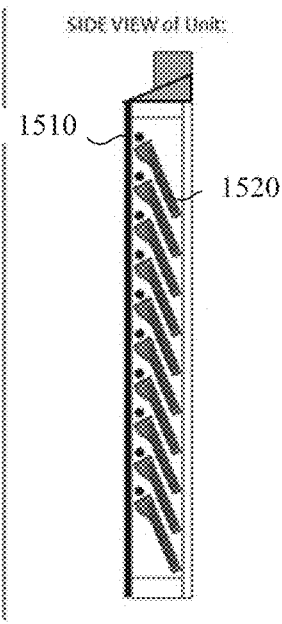
Figure 15B:
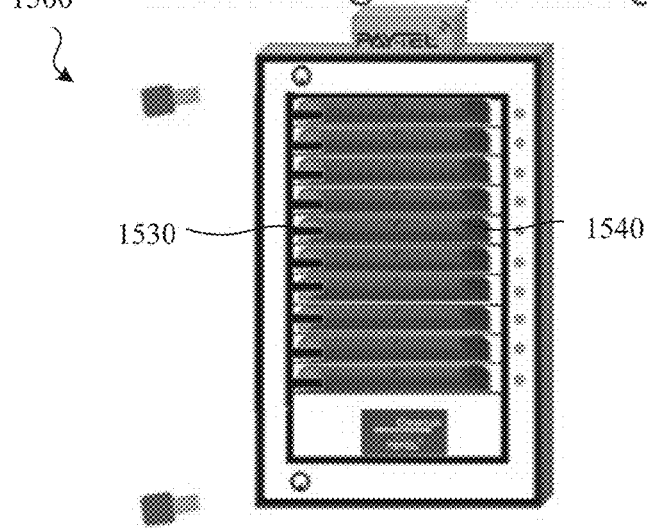
Figure 15B:
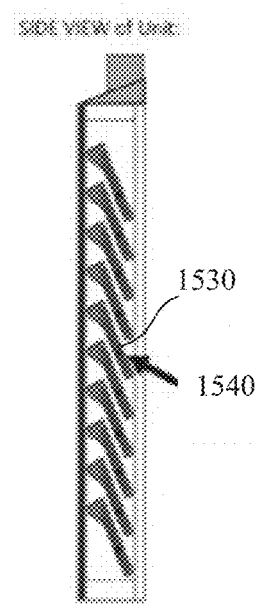
Figure 16:
FIG. 16 is a rear view of an exemplary electronic device capable of being charged via a charging station.
Figure 17:
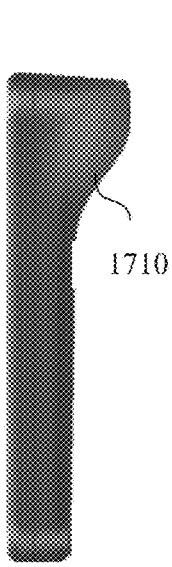
FIG. 17 is a side view of the electronic device of FIG. 16.
Figure 18:
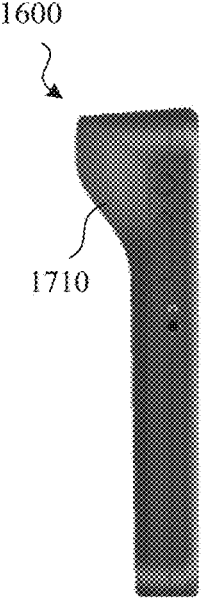
FIG. 18 is a side view of the electronic device of FIG. 16.
Figure 19:
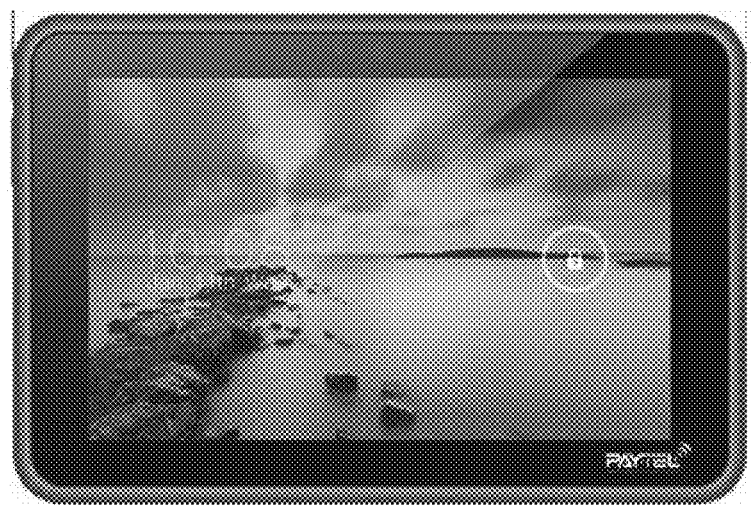
FIG. 19 is a front view of the electronic device of FIG. 16.

FIGS. 15A and 15B are block diagrams illustrating locking pin-based locking mechanism of a charging station 1500. In the example of FIG. 15A, each locking pin (e.g., locking pin 1510) is configured to extend just above a respective electronic device (e.g., electronic device 1520) to prevent the electronic device from being removed when the locking pin is in a locked position. When unlocked, the locking pin 1510 is retracted (e.g., into the charging station 1500) and thus does not obstruct the electronic device 1520 from being removed.

In the example of FIG. 15B, each locking pin (e.g., locking pin 1530) is configured to extend just into a side of a respective electronic device (e.g., electronic device 1540) to prevent the electronic device from being removed when the locking pin is in a locked position. For example, the locking pin 1530 could be inserted into a reinforced opening formed in an electronic device such as into reinforced opening 2010 of electronic device 1540 depicted in FIGS. 20 and 21. When unlocked, the locking pin 1510 is retracted (e.g., into the charging station 1500) and thus does not obstruct the electronic device 1520 from being removed.

Locking can be accomplished by a pin system that flips once to allow the addition of another electronic device.

In another implementation, a charging station includes a door to lock one or more of the electronic devices or for other storage purposes (e.g., usable by staff only to store their personal phones, an emergency cell phone, etc.) The locking system may provide an option to have a locking cover so no electronic devices can be accessed until allowed by service provider employee or other authorized person. A locking lever, automated lock, or other locking mechanism may be on either side of the charger as well as on the front of the charger. An additional external cover may be used to entirely cover the station to prevent access of any kind.

A charging station may be configured with various other features. A charging station may be configured to drive a remote TV, or monitor with other information. A charging station may be used as a hot spot or AP connection. A charging station may provide a data connection or store data for other electronic devices. A charging station may have other smart functions that allow communication to all the electronic devices, or from all the electronic device, with software/feature updates/special controls. A charging station may have USB and other connections to allow for data/information/services/RFID/bar code scanning/eye scan/finger print. In some implementations, the charging station receives information from the electronic devices that it charges when those devices are separated from the charging station (e.g., out in the confinement institution POD). In some implementations, information from the electronic devices is used to triangulate or otherwise determined the locations of those devices.

In some implementations, a charging station is configured to automatically connect to the electronic device when the electronic device is placed in the charging station. Plugs or wires can, but need not be used for power or data transmission between the charging station and the electronic device. This can simplify the charging or updating of electronic devices. In some implementations, a charging station is used as a combined charger/USB/data device that can charge multiple tablets (or other electronic devices) and connect with the electronic devices to do updates, uploads, and other data-intensive data transfers.

In some implementations, a charging station is configured to charge multiple devices of different types, e.g., both tablets and laptops, both tablets and mobile phones, etc., or devices of a same type but of different sizes, e.g., tablets with 8 inch screens and tablets with 10 inch screens, etc.

In some implementations, one of the electronic devices in the charging unit is in a fixed position/not removable and can only be used for specific functions (i.e., ordering commissary, video calls, etc.). Such a device can provide an interface for the charging station monitoring and management functions. In other implementations, any of the electronic devices, given proper authorized user authorization, can be used as an input/output interface for the charging station monitoring and management functions.

In some implementations, a charging station has a handset, speaker, or display for general user features such as staff announcements, music, video, time display, etc. A charging station could support ADA requirements by allowing video relay services through it for the hearing impaired. In some implementations, an ear bud or other listening device is attached to a charging station and the inmates are enabled to perform calls or video calls using the charger. A charging station may have a microphone that allows an inmate to call for help, for example, responding automatically to particular words ("help," "guard," "fire,") etc.

In some implementations, a charging station includes ruggedized components, e.g., components that include rubber or shock absorbing surfaces or reinforced components.

A charging station may have slanted side vents, no vents on the top, louvers added to the vents, drain holes in the bottom of the charging station, and/or other features that facilitate venting while prohibiting fluid entry. In some implementations, a charging station includes a vapor barrier at the back to prohibit the entry of moisture from behind the charging station.

In some implementations, a charging station includes a battery backup. If the electricity goes out, the battery on the charging station can act like a UPS and an indicator light can provide emergency lighting to the POD or other confinement facility area. Similarly, a charging station can be configured with connectivity to the electronic devices even in power outage circumstances to ensure that calls/messaging/communications can continue when the power is out. In another example, the charging station may be configured to send notifications to the inmates during a power out emergency.

In some implementations, the charging station has a slanted or sloped top or cap (see, for example, the side views in FIGS. 14 and 15) to prevent or discourage inmates from placing drinks on top of the charging stations. The slanted or sloped top can be part of the charging station body or be provided by a cap or other add-on component. The slope on the top of the charging station can prevent or discourage inmates from putting things on top of the charging station that contain liquids, small objects, or other undesirable substances and thus reduce the risk of damage to the internal parts of the charging station. The charging station may have channels that would allow liquids and small objects to pass through the charging bays/slots and a sloped top may reduce the risk of such intrusions. In other implementations, the top of the charging station has alternative geometries (e.g., curved) other than horizontal to prevent or discourage inmates from resting objects on top.

In some implementations, a charging station includes antibacterial lights positioned to illuminate one or more of the electronic devices during charging or otherwise while the electronic devices are inserted within the charging station. In one example, the charging station includes a germicidal lamp that produces ultraviolet light. The short-wave ultraviolet light disrupts DNA base pairing causing formation of pyrimidine dimers and lead to the inactivation of bacteria, viruses, and protozoa.

In some implementations, the charging station includes one or more indicators. For example, the charging station may be configured to trigger an alarm based on detecting an intrusion. In some implementations, the charging station includes an indicator (e.g., light, speaker, etc.) that provides an audible or visual indication when a device has been seated correctly or correctly locked. In some implementations, the charging station includes an alarm that is triggered when an attempt is detected to remove an electronic device during restricted times or when the electronic device is locked at the charging station.

In some implementations, the charging station is configured to lock or otherwise prevent removal of an electronic device unless the electronic device is charged to a particular degree, e.g., 75% charged, fully charged, etc. Similarly, removal of the electronic device may be prevented while the electronic device is receiving updates or when an electronic device fault or error has been detected.

In some implementations, the charging station is configured to assess the status or condition of an electronic device when the electronic device is returned. For example, the charging station may run a diagnostic on a returned electronic device capture an image of the returned electronic device and analyze the image to identify damage (e.g., broken screens, etc.), or otherwise assess the status or condition of the electronic device. In one example, an image of the device is captured when the device is checked out or removed and compared with an image of the device when the device is checked in or returned.

Is some implementations, user-specific data and use history on each of the electronic devices is automatically erased when the electronic device is checked in or returned to the charging station. In some implementations, a copy of user-specific data is captured and stored on a server or other storage device for later use by the particular user or review by officers, investigators, law enforcement, or other persons.

In some implementations, the charging station is part of a system that facilitates management of electronic devices. In one implementation, the system receives an inmate identifier and a device identifier when the inmate removes a device from the charging station. For example, the inmate may enter an inmate ID and password or otherwise provide login/identification credentials. The charging station may track the removal of a particular device, e.g., based on tracking which devices are in which slot or based on communicating with the electronic device that is removed.

When an inmate returns a tablet or other electronic device to the charging station, the system again recognizes the event. For example, the charging station may identify the particular electronic device that is returned to the charging station based on communicating with the electronic device or using information provided by the inmate, or both. Accordingly, at any given time, e.g., at the end of the day, facility officers are able to access the system to determine which inmates still have electronic devices outstanding and identify any missing electronic devices without having to perform manual inspections. The system replaces the error prone and burdensome manual tracking processes that would otherwise be required with an efficient and accurate automated electronic device tracking process.

The charging station may be configured to send wireless communications to the electronic devices to cause the electronic devices to discontinue operation and/or to present messages. In some implementations, device usage is restricted to particular hours, e.g., until 8 pm, and a message is sent to electronic devices at or before the end of the usage period instructing the inmates to return the electronic devices to the charging station. In some implementations, a message is sent to a particular electronic device or particular group of electronic devices to inform the respective users of a particular message. For example, all devices checkout out to inmates in a particular POD may receive a message that lunch is starting.

Numerous specific details are set forth herein to provide a thorough understanding of the claimed subject matter. However, those skilled in the art will understand that the claimed subject matter may be practiced without these specific details. In other instances, methods apparatuses, or systems that would be by one of ordinary skill have not been described in detail so as not to obscure claimed subject matter.

Some implementations provide multiple charging stations that can be connected to one another (e.g., physically and electrically) to provide easily scalable multi-device charging. For example, each charging station can be configured to charge 10 devices. One charging station can be used to charge 10 electronic devices, two connected charging stations can be connected to charge 20 electronic devices, three connected charging stations can be connected to charge 30 electronic devices, etc. The first charging station electrically plugs into a power outlet or is hardwired to an intra-wall electrical wire via a wall opening behind the charging station (e.g., through a hole in the wall). The additional charging stations plug into the first charging station or one another (e.g., in a chain configuration, a hub and spoke configuration, etc.) or directly to an outlet or intra-wall connection. In some implementations, multiple charging stations are connected via a hidden conduit between the units.

In some implementations, the charging station includes an outer case that protects the electronic devices from access and damage. The outer case may be configured to be entirely removed, partially removed, or moved to expose the electronic devices for access by the inmates and other users. Such an outer case may include a sliding portion (see FIG. 6 for examples of a sliding portions on mobile charging station units) or a hinged portion that allows the outer case to move to expose the electronic devices for access and return. In one example, hinges connect an outer case to a body of the charging station, e.g., configured to allow the outer case to be raised and lowered.

Exemplary Electronic Devices

FIGS. 16-19 illustrate an exemplary electronic device configured for use with a charging station and/or in a confinement institution. The example electronic device 1600 is configured to be oriented at an angle relative to a flat surface upon which it is rested. The bump portion 1710 is shaped such that, when the electronic device 1600 is laid face up, i.e., with its underside resting on a horizontal underlying surface, the bump portion 1710 will cause the device screen to sit at a non-horizontal angle. The screen will be tilted up to enable easier viewing by an inmate or other user, without requiring the inmate/user to hold the device at such an angle. The bump portion, in some implementations, thus serves to both ensure proper insertion/alignment in the charging station and facilitate a better resting display angle for the electronic device.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the disclosure are to be understood as being in every respect illustrative and exemplary, but not restrictive, and the scope of the disclosure disclosed herein is not to be determined only from the detailed description of illustrative implementations but according to the full breadth permitted by patent laws. It is to be understood that the implementations shown and described herein are only illustrative of the principles of the present disclosure and that various modification may be implemented by those skilled in the art without departing from the scope and spirit of the disclosure.

What is claimed is:

1. A method comprising:

at a computing device comprising a processor:

identifying a charging station event at a charging station, the charging station event involving a user removing an electronic device from a receiving portion of the charging station or the user returning the electronic device to the receiving portion of the charging station;

identifying the electronic device involved in the charging station event;

identifying the user involved in the charging station event; and tracking use of the electronic device based on identifying the electronic device and the user involved in the charging station event.

2. The method of claim 1, wherein the charging station comprises multiple receiving portions for charging multiple electronic devices simultaneously.

3. The method of claim 1, wherein the charging station event involves the user removing the electronic device from the receiving portion of the charging station.

4. The method of claim 1, wherein the charging station event involves the user returning the electronic device to the receiving portion of the charging station.

5. The method of claim 1, wherein identifying the charging station event is based on detecting a connecting or a disconnecting of a power transfer connection at the receiving portion.

6. The method of claim 1, wherein identifying the electronic device is based on a scan of an identifier on the electronic device.

7. The method of claim 1, wherein identifying the electronic device is based on a computer vision object detection of an image of the electronic device.

8. The method of claim 1, wherein identifying the electronic device is based on detecting that the electronic device has changed communication status from disconnected to connected or connected to disconnected within a charging event time window.

9. The method of claim 1, wherein identifying the electronic device comprising:

monitoring the charging status of a plurality of electronic devices; and identifying that the electronic device is the only electronic device of the multiple electronic devices to change charging status within a charging event time window.

10. The method of claim 1, wherein identifying the electronic device is based on a communication received from the electronic device, the communication identifying the electronic device.

11. The method of claim 1, wherein identifying the user comprises receiving a user identifier input at the charging station.

12. The method of claim 1, wherein identifying the user comprises receiving a user identifier input at the electronic device.

13. The method of claim 1, wherein identifying the user is based on an image of the user captured by a camera on the charging station within an event time window.

14. The method of claim 1, wherein identifying the user is based on an image of the user captured by a camera on the electronic device within an event time window.

15. The method of claim 1, wherein identifying the user is based on performing computer vision-based face detection on an image of the user.

16. The method of claim 1, wherein identifying the user is based on a three dimensional model of the user obtained from an infrared projector and camera.

17. The method of claim 1, wherein identifying the user is based on a fingerprint or eye scan of the user.

18. The method of claim 1, wherein identifying the user is based on a sound recording of a voice of the user.

19. The method of claim 1 further comprising providing visual or audible instructions on the electronic device or charging station to guide the user to capture an image of the user or an image of the electronic device.

20. The method of claim 1 further comprising detecting a condition of the electronic device based on an image of the electronic device.

21. The method of claim 1, wherein tracking the use of the electronic device comprises determining a period of time that the electronic device was used by the user based on a check-out charging station event and a check-in charging station event.

22. The method of claim 1, wherein tracking the use of the electronic device comprises determining a change in condition of the electronic device based on a first condition of the electronic device at a check-out charging station event and a second condition of the electronic device at a check-in charging station event.

23. The method of claim 22, wherein the first condition and second condition are determined based on images of the electronic device.

24. The method of claim 22, wherein the first condition and second condition are determined using a machine learning model on images of the electronic device.

* * * * *